US012686872B2

(12) United States Patent
Zhang et al.

(10) Patent No.: US 12,686,872 B2
(45) Date of Patent: Jul. 21, 2026

(54) METHOD FOR BOOSTING GENETIC TRANSFORMATION EFFICIENCY OF WHEAT USING AGROBACTERIUM-MEDIATED METHOD

(71) Applicant: Shandong Agricultural University, Tai'an City (CN)

(72) Inventors: Xiansheng Zhang, Tai'an City (CN); Xiaomin Bie, Tai'an City (CN); Menglu Li, Tai'an City (CN); Yanyan Chang, Tai'an City (CN); Ying Song, Tai'an City (CN)

(73) Assignee: SHANDONG AGRICULTURAL UNIVERSITY, Tai'an City (CN)

( * ) Notice: Subject to any disclaimer, the term of this patent is extended or adjusted under 35 U.S.C. 154(b) by 0 days.

(21) Appl. No.: 19/010,526

(22) Filed: Jan. 6, 2025

(65) Prior Publication Data

US 2026/0117238 A1     Apr. 30, 2026

(30) Foreign Application Priority Data

Oct. 30, 2024     (CN) .......................... 202411526596.9

(51) Int. Cl.
*C12N 15/82*          (2006.01)

(52) U.S. Cl.
CPC ................................ *C12N 15/8205* (2013.01)

(58) Field of Classification Search
CPC .............. C12N 15/8205; C12Q 1/6895; C12Q 2600/13; Y02A 40/146; C07K 14/195; C07K 14/415; A01H 1/12; A01H 4/006; C12R 2001/01; A01G 7/00; A01G 22/00
See application file for complete search history.

(56) References Cited

U.S. PATENT DOCUMENTS

| | | | |
|---|---|---|---|
| 7,993,914 B2 | 8/2011 | Ito et al. | |
| 2006/0150283 A1* | 7/2006 | Alexandrov | ......... C07K 14/415 536/23.6 |

FOREIGN PATENT DOCUMENTS

WO     WO-2021030242 A1 *  2/2021  ......... C12N 15/8233

OTHER PUBLICATIONS

Hayta et al., 2019, An efficient and reproducible Agrobacterium-mediated transformation method for hexaploid wheat (*Triticum aestivum* L.). Plant Methods. 15:121. (Year: 2019).*

Li et al. (2012). Genetic diversityamong a founder parent and widely grown wheat cultivars derived from the same origin based on morphological traits and microsatellite markers. Crop & Pasture Science. 63:303-310. (Year: 2012).*

Thompson, C. J., Movva, N. R., Tizard, R., Crameri, R., Davies, J. E., Lauwereys, M., & Botterman, J. (Sep. 1987). Characterization of the herbicide-resistance gene bar from *Streptomyces hygroscopicus*. The EMBO journal, 6(9), 2519-2523.

BlpR. (Accessed Mar. 5, 2026). https://www.molecularcloud.org/part/BlpR/402.html.

Browne, W. J., North, A. C. T., Phillips, D. C., Brew, K., Vanaman, T. C., & Hill, R. L. (May 1969). A possible three-dimensional structure of bovine α-lactalbumin based on that of hen's egg-white lysozyme. Journal of molecular biology, 42(1), 65-86.

* cited by examiner

*Primary Examiner* — Bratislav Stankovic
*Assistant Examiner* — Emily K Johnson
(74) *Attorney, Agent, or Firm* — Tutunjian & Bitetto, P.C.

(57)     ABSTRACT

Disclosed is a method for boosting genetic transformation efficiency of wheat using an *Agrobacterium*-mediated method, which belongs to the field of plant genetic engineering technology. A TaHRF2 gene and an encoded protein thereof used in the present disclosure can promote introduction of a nucleic acid molecule into a plant of interest and boost genetic transformation efficiency of the introduction of the nucleic acid molecule into the plant of interest. The plant of interest includes, but is not limited to, monocotyledonous plants such as wheat. By introducing a TaHRF2 gene high-expression vector into an *Agrobacterium* strain, and infecting a wheat explant using an *Agrobacterium*-mediated method, genetic transformation capacities of backbone parents such as Beijing 8 and Lumai 1 are enhanced, providing important information and fundamental technical support for the establishment of an efficient genetic transformation system for major wheat cultivars with difficulty in regeneration.

4 Claims, 4 Drawing Sheets

Specification includes a Sequence Listing.

METHOD FOR BOOSTING GENETIC TRANSFORMATION EFFICIENCY OF WHEAT USING AGROBACTERIUM-MEDIATED METHOD

CROSS REFERENCE TO RELATED APPLICATION

This patent application claims the benefit and priority of Chinese Patent Application No. 202411526596.9 filed with the China National Intellectual Property Administration on Oct. 30, 2024, the disclosure of which is incorporated by reference herein in its entirety as part of the present application.

REFERENCE TO SEQUENCE LISTING

A computer readable XML file entitled "GWP20241107298", that was created on Dec. 16, 2024, with a file size of about 15,031 bytes, contains the sequence listing for this application, has been filed with this application, and is hereby incorporated by reference in its entirety.

TECHNICAL FIELD

The present disclosure relates to the field of plant genetic engineering technology, and particularly relates to a method for promoting the genetic transformation of wheat using an *Agrobacterium*-mediated method.

BACKGROUND

*Agrobacterium* is a ubiquitous microorganism in the soil. Two types of *Agrobacterium, Agrobacterium tumefaciens* and *Agrobacterium rhizogenes*, have been widely used by researchers. They can infect wounded parts of plants and induce host plants to produce crown gall tumors or hairy roots. *Agrobacterium tumefaciens* containing a tumor-inducing plasmid (Ti plasmid) can induce a host cell to produce a crown gall tumor, while *Agrobacterium rhizogenes* carrying a root-inducing plasmid (Ri plasmid) induces a plant cell to produce a hairy root, both of which contain a T-DNA region. After *Agrobacterium* enters plant cell by infecting a wound of plant, T-DNA can be inserted into a genome of the plant and can be stably passed on to the offspring through meiosis. The transfer and integration of an exogenous gene into a plant cell can be achieved by means of the *Agrobacterium* infection, and a transgenic plant is then regenerated by tissue culture techniques. The *Agrobacterium*-mediated transformation method has a wide range of applications. More than 80% of transgenic plants are mediated by *Agrobacterium tumefaciens*, which has the advantages genetic stability, easy transformation of large DNA fragments, simple operation, etc. Currently, genetic transformation systems have been established in a variety of crops, such as rice (Nishimura, 2020), maize (Masters et al., 2020), wheat (Ye et al., 2023), cotton (Zhang, 2019), and soybean (Li et al., 2017).

Common wheat, as an allohexaploid, is one of the most important sources of food in many countries around the world, providing humans with about above 20% of their energy. Due to the large genome and complex chromosome inheritance of wheat, there is a plurality of copies for the vast majority of genes. Therefore, it is difficult to satisfy the analysis of functions of wheat genes and the improvement of agronomic traits by using traditional breeding methods. As a result, the research on wheat bio-breeding lags far behind that of other food crops such as maize and rice. The growing maturity of transgenic technology and gene editing technology provides technical support for bio-breeding. However, the vast majority of wheat genotypes have low genetic transformation efficiency, long time for obtaining transgenic plant, and strong genotype dependence. These are major obstacles to study gene functions and promote the development of bio-breeding of wheat. Therefore, boosting the genetic transformation efficiency of wheat is essential for genetic function research and genetic improvement and breeding of crops.

SUMMARY

Aiming at the prior art described above, an objective of the present disclosure is to provide a method for boosting genetic transformation efficiency of wheat using an *Agrobacterium*-mediated method.

In order to achieve the objective described above, the present disclosure adopts the following technical solutions.

In a first aspect of the present disclosure, provided is use of a TaHRF2 gene in any one of (1) to (3) as follows:

(1) boosting transformation efficiency of integration of a nucleic acid molecule into a genome of wheat;
  (2) boosting regeneration efficiency of a wheat plant;
  (3) cultivating a transgenic and gene-edited wheat plant.
  The TaHRF2 gene is a DNA molecule as shown in i) or ii) below:
  i) a DNA molecule having a nucleotide sequence set forth in SEQ ID NO. 1;
  ii) a DNA molecule encoding an amino acid sequence set forth in SEQ ID NO. 2, excluding i).
  Preferably, in the use described above, a variety of the wheat is "Beijing 8" or "Lumai 1".

In a second aspect of the present disclosure, provided is use of a protein encoded by a TaHRF2 gene in any one of (1) to (3) as follows:

(1) boosting transformation efficiency of integration of a nucleic acid molecule into a genome of wheat;
  (2) boosting regeneration efficiency of a wheat plant;
  (3) cultivating a transgenic and gene-edited wheat plant.
  Preferably, the protein encoded by the TaHRF2 gene is a protein as shown in (A1) or (A2) below:
  (A1) a protein consisting of an amino acid sequence set forth in SEQ ID NO. 2 of the Sequence Listing;
  (A2) a fusion protein obtained by attaching a protein tag to the N-terminus and/or the C-terminus of the protein defined in (A1).

In a third aspect of the present disclosure, provided is use of an expression cassette, recombinant expression vector or recombinant bacterium containing a TaHRF2 gene in any one of (1) to (3) as follows:

(1) boosting transformation efficiency of integration of a nucleic acid molecule into a genome of wheat;
  (2) boosting regeneration efficiency of a wheat plant;
  (3) cultivating a transgenic and gene-edited wheat plant.
  In a fourth aspect of the present disclosure, provided is a method for boosting transformation efficiency of wheat using an *Agrobacterium*-mediated method, the method including the following steps:
  ligating a TaHRF2 gene into an expression vector to construct a recombinant expression vector, and transforming the recombinant expression vector into an *Agrobacterium* competent cell to obtain an *Agrobacterium* strain for transformation;

infecting immature embryo of a wheat with the *Agrobacterium* strain, thereby boosting transformation efficiency and obtaining a transgenic and gene-edited wheat plant.

Preferably, the expression vector is a pUbi110 plasmid.

Preferably, the *Agrobacterium* competent cell is *Agrobacterium* EHA105.

The present disclosure has the following beneficial effects.

It has been found for the first time in the present disclosure that a TaHRF2 gene can boost the transformation efficiency of introduction of a target nucleic acid molecule into a plant of interest and/or promote the introduction of the nucleic acid molecule into the plant of interest by an *Agrobacterium*-mediated method. The plant of interest includes, but is not limited to, monocotyledonous plants such as wheat. A high-expression vector is constructed using a CDS sequence of the TaHRF2 gene, and introduced into an *Agrobacterium* strain, with which wheat immature embryos are infected. The results show that the TaHRF2 high-expression vector promotes the entry of the target nucleic acid molecule into the plant of interest compared with a control vector. The use of a TaHRF2 gene can boost the genetic transformation efficiency of integration of a target gene into a genome of a plant, which in turn increases genetic transformation capacities of backbone varieties such as Beijing 8 and Lumai 1, providing important information and fundamental technical support for the establishment of an efficient genetic transformation system of major wheat cultivars with difficulty in regeneration, and resulting in important economic value and social benefits.

BRIEF DESCRIPTION OF THE DRAWINGS

FIG. 3A shows Beijing 8 transformed with a pUbi110-GUS vector; FIG. 3B shows Beijing 8 transformed with a pUbi110-TaHRF2 vector;

FIG. 3C shows Lumai 1 transformed with a pUbi110-GUS vector; FIG. 3D shows Lumai 1 transformed with a pUbi110-TaHRF2 vector;

DETAILED DESCRIPTION OF THE EMBODIMENTS

Figure 1:
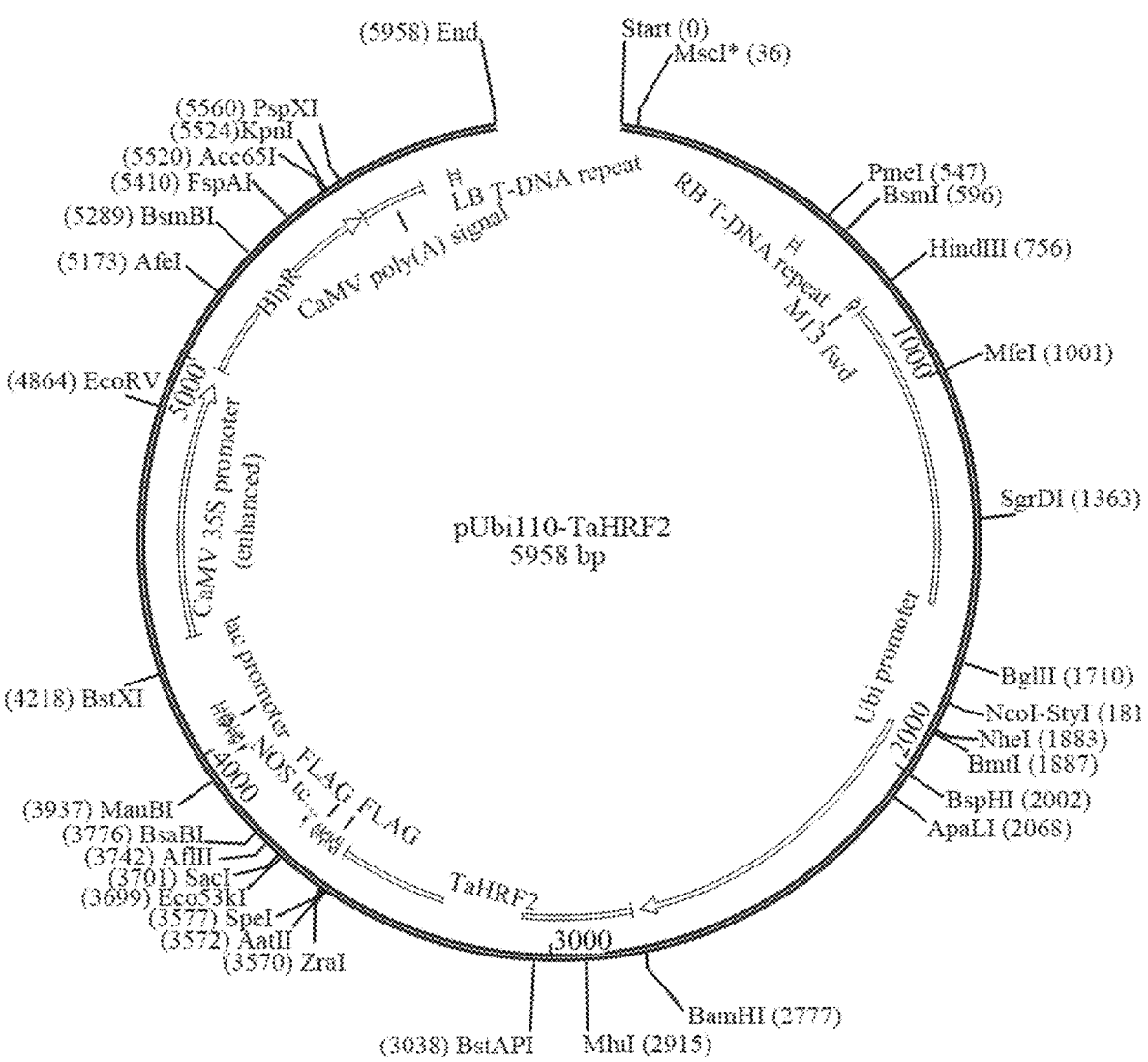
FIG. 1 shows a vector structure diagram of a plant expression vector pUbi110-TaHRF2.

It should be noted that following detailed description is exemplary and is intended to provide further illustration of the present application. Unless otherwise indicated, all technical and scientific terms used herein have the same meaning as commonly understood by those of ordinary skill in the art to which the present application belongs.

As described above, the low genetic transformation efficiency and strong genotype dependence are major obstacles restricting the research and application of gene functions of wheat.

The number of regeneration genes of wheat that have been isolated and identified so far remains very small, and there are still many major cultivars and backbone parents of wheat that cannot be successfully transformed.

"Beijing 8" is a wheat variety bred under the chairmanship of academician ZHUANG, Qiao Sheng, a researcher from the Institute of Crop Science, Chinese Academy of Agricultural Sciences. It has the advantages of early maturity, rust resistance, high yield and good quality. "Lumai 1" is a wheat variety selected and bred by Shandong Agricultural University. It has high resistance to stripe rust, and has resistance to leaf rust, stem rust and powdery mildew, resistance to lodging, resistance to dry and hot winds, and good leaf senescence and yellowing. Both wheat varieties have now been withdrawn from the market, but as wheat varieties used to be popularized in large areas, dozens of wheat varieties have been bred with them as parents, and they still have good application prospects as breeding base materials for genetic improvement.

However, "Beijing 8" and "Lumai 1" are among the most difficult wheat varieties to transform, making it difficult to undergo transgenic integration and gene editing.

Based on this, in-depth research has been conducted in the present disclosure on the genetic transformation of "Beijing 8" and "Lumai 1," and the results show that by transferring a TaHRF2 gene derived from wheat into the wheat varieties "Beijing 8" or "Lumai 1" using an *Agrobacterium*-mediated method, the genetic transformation efficiency of these two extremely difficult-to-transform wheat varieties can be significantly increased.

A nucleotide sequence of the TaHRF2 gene is as set forth in SEQ ID NO. 1, and an amino acid sequence of a protein encoded by the TaHRF2 gene is as set forth in SEQ ID NO. 2; specifically as follows:

```
TaHRF2 gene:
                                (SEQ ID NO. 1)
ATGGCGGCGACGGCGACTGCGACGGCGGCGGCGACGAGCGTGGTG

ACGGGGACGACGCGGTGGTGCCCGACGCCGGAGCAGCTGATGATC

CTGGAGGAGATGTACCGCGGCGGGCTGCGCACCCCCAACGCGTCG

CAGATCCAGCAGATCACGGCGCACCTGGCCCACTACGGCCGCATC

GAGGGCAAGAACGTCTTCTACTGGTTCCAGAACCACAAGGCCCGG

GACCGCCAGAAGCTCCGCCGCAGGCTCTGCATGAGCCACCACCTC

CTCTCCTGCGCGCACTACTACGCCGCCGCCAACGCCGGCCAGTAC

CACCAGCAGCAGCAGCTCCTCGGCGCCGGCGCGGTGCCTCCTCCG

CTGCTGCAGCACCCGCAGCAGCAGCAGTACTACTCCGCCTCTTGC

GCCGGTGGCGGCTACGACCAGCACCTGCTCCCGACGACCGTCCCA

GCTTCCGCTTACGCTGCTGCTGCTGGGTACGCCTACCCCTTCGCC

GGCGTGCCGGCAAGCCGGTGCGCCGAGCCCTCGCCGCCAAACACC

CCGCTCTCCTTCCATCATCAGGGAGGAGGCGTAGTGGGATCGCCG
```

-continued

```
GAGTACTCGCTGGGGAGGCTGGGCAACTTCGGCGTGGTGGAGGAC

ACATGCCGGCCGTCGCGGTACGAGCAGCAGCCGCAGCAGCTGGCC

GCGGCGACGGAAGATCAGGCGGCGCCGGTGACGGCGACGGGGCTG

TTCTGCCGGCCGCTGAAGACGCTGGACCTCTTCCCCGGCGCGATC

AAGGAGGAGCAGCGCGACGTCGCCTAG

Protein encoded by the TaHRF2 gene:
                                (SEQ ID NO. 2)
MAATATATAAATSVVTGTTRWCPTPEQLMILEEMYRGGLRTPNAS

QIQQITAHLAHYGRIEGKNVFYWFQNHKARDRQKLRRRLCMSHHL

LSCAHYYAAANAGQYHQQQQLLGAGAVPPPLLQHPQQQQYYSASC

AGGGYDQHLLPTTVPASAYAAAAGYAYPFAGVPASRCAEPSPPNT

PLSFHHQGGGVVGSPEYSLGRLGNFGVVEDTCRPSRYEQQPQQLA

AATEDQAAPVTATGLFCRPLKTLDLFPGAIKEEQRDVA
```

In order to enable those skilled in the art to have a clearer understanding of the technical solutions of the present application, the technical solutions of the present application will be described in detail below in connection with specific examples.

The test materials used in the examples of the present disclosure, which are not specified, are conventional test materials in the field and are all commercially available. In the present disclosure, an expression vector is introduced into a plant cell. Methods of introduction are well known to those skilled in the art, including, but not limited to: an *Agrobacterium*-mediated method, a gene gun bombardment method, a pollen tube pathway method, an electroporation method, and an ovary injection method. A selectable marker gene used in the present disclosure is a bar gene, which encodes a phosphinothricin acetyltransferase PAT protein. Other selectable marker genes and reporter genes such as nptII and hpt can be further used. A screening antibiotic selected in the present disclosure is phosphinothricin, and screening agents such as bialaphos can also be selected to achieve the same effect. Where specific experimental conditions and methods are not indicated in the examples of the present disclosure, conventional conditions, such as those described in J. Sambrook et al., eds., Science Press, 2002, Molecular Cloning: A Laboratory Manual (Third Edition); D. L. Speckt et al., eds., Science Press, 2001, Cells: A Laboratory Manual; or conditions recommended by the manufacturer are generally followed.

Example 1: Construction of Recombinant Expression Vectors

1. Construction of a Recombinant Expression Vector pUbi110-TaHRF2:

Total RNA was extracted from a wheat material Fielder using an Ultrapure RNA Kit (CWBIO, catalog number: CW0581M).

By referring to a HiScript® II 1st Strand cDNA Synthesis Kit (+gDNA wiper) kit (Nanjing Vazyme Biotech Co., Ltd., catalog number: R212), reverse transcription was performed to obtain cDNA.

Taking cDNA as a template, PCR amplification was performed using a primer pair (upstream primer: 5'-ATGGCGGCGACGGCGACTG-3' (SEQ ID NO:3); downstream primer: 5'-CTAGGCGACGTCGCGCTGC-3' (SEQ ID NO:4)). An amplification system consisted of 2 μl of upstream primer (10 μmol/μl), 2 μl of downstream primer (10 μmol/μl), 12.5 μl of 2× Phanta Max Master Mix, 1 μl of cDNA template, and a balance of ddH₂O to 25 μl. Amplification conditions were: predenaturation at 95° C. for 5 minutes; denaturation at 95° C. for 30 seconds, annealing at 59° C. for 30 seconds, extension at 72° C. for 30 seconds, for 38 cycles; extension at 72° C. for 5 minutes.

The amplified PCR product was ligated into a pEASY®-Blunt3 vector by referring to operation steps of a pEASY®-Blunt3 Cloning Kit (TransGen Biotech Co., Ltd., Beijing, catalog number: CB301-01) to obtain a pEASY-Blunt3-TaHRF2 vector, and sequencing was performed.

Single restriction endonuclease cleavage sites (SmaI, SpeI) on an overexpression vector pUbi110 were selected for the enzyme cleavage of the vector. The enzyme cleavage products were subjected to gel recovery by referring to a FastPure Gel DNA Extraction Mini Kit (Nanjing Vazyme Biotech Co., Ltd., catalog number: DC301-01).

Taking a pEASY-Blunt3-TaHRF2 plasmid as a template, PCR amplification was performed with a homogeneous primer pair designed (upstream primer: 5'-CGACTCT AGAGGATCCCCGGGATGGCGGCGACGGCGACT-3' (SEQ ID NO:5); downstream primer: 5'-GAAT-TCCGGCTCGAGACTAGTCTAGGCGACGTC GCG CTG-3' (SEQ ID NO: 6)). An amplification system consisted of 2 μl of upstream primer (10 μmol/μl), 2 μl of downstream primer (10 μmol/μl), and 12.5 μl of 2× Phanta Max Master Mix, 1 μl of cDNA template, with ddH₂O added to bring the total volume up to 25 μl. Amplification conditions were: predenaturation at 95° C. for 5 minutes; denaturation at 95° C. for 30 seconds, annealing at 59° C. for 30 seconds, extension at 72° C. for 30 seconds, for 38 cycles; extension at 72° C. for 5 minutes.

The amplified PCR product was ligated to an enzyme cleavage product of a pUbi110 vector by referring to homologous recombination steps of LightNing™ DNA Assembly Mix Plus (BestEnzymes Biotech Co., Ltd.), and sequencing was performed. Plasmids were extracted from monoclonal colonies with correct sequencing by referring to a FastPure Plasmid Mini Kit (Nanjing Vazyme Biotech Co., Ltd., catalog number: DC201-01), and a recombinant expression vector pUbi110-TaHRF2 was obtained. A schematic diagram of part of the structure of the vector is as shown in FIG. 1.

2. Construction of a Control Vector pUbi110-GUS:

By referring to nucleotides at positions 15108-16919 of Gene ID: MN266288.1 on the NCBI (www.ncbi.nlm.nih-.gov/) website, PCR amplification was performed using a primer pair (upstream primer: 5'-ATGTTACGTCC TGTAGAA-3' (SEQ ID NO:7); downstream primer: 5'-TCATTGTTTGCCTCCCTG-3' (SEQ ID NO:8)). An amplification system consisted of 2 μl of upstream primer (10 μmol/μl), 2 μl of downstream primer (10 μmol/μl), 12.5 μl of 2× Phanta Max Master Mix, 1 μl of eDNA template, and a balance of ddH2O to 25 μl, Amplification conditions were; predenaturation at 95° C. for 5 minutes; denaturation at 95° C. for 30 seconds, annealing at 58° C. for 30 seconds, extension at 72° C. for 1 minute, for 38 cycles; extension at 72° C. for 5 minutes.

The amplified PCR product was ligated by referring to operation steps of a pEASY®-Blunt3 Cloning Kit (catalog number: CB301-01, TransGen Biotech Co., Ltd., Beijing) to obtain pEASY-Blunt3-GUS, and sequencing was performed for verification. Upon the sequencing analysis, the PCR product was the GUS gene.

Taking pEASY-Blunt3-GUS as a template, PCR amplification was performed with a primer pair designed (upstream primer: 5'-CGACTCTAGAGGATCCCCGGGATGTTA CGTCCTGTAGAAACCCCA-3' (SEQ ID NO: 9); downstream primer: 5'-GAATTCCGGCTCGAGACTAGTTT GTTTGCCTCCCTGCTGC-3' (SEQ ID NO:10)). An amplification system consisted of 2 μl of upstream primer (10 μmol/μl), 2 μl of downstream primer (10 μmol/μl), 12.5 μl of 2× Phanta Max Master Mix, 1 μl of cDNA template, and a balance of ddH₂O to 25 μl. Amplification conditions were:

predenaturation at 95° C. for 5 minutes; denaturation at 95° C. for 30 seconds, annealing at 58° C. for 30 seconds, extension at 72° C. for 1 minute, for 38 cycles; extension at 72° C. for 5 minutes.

Figure 2:
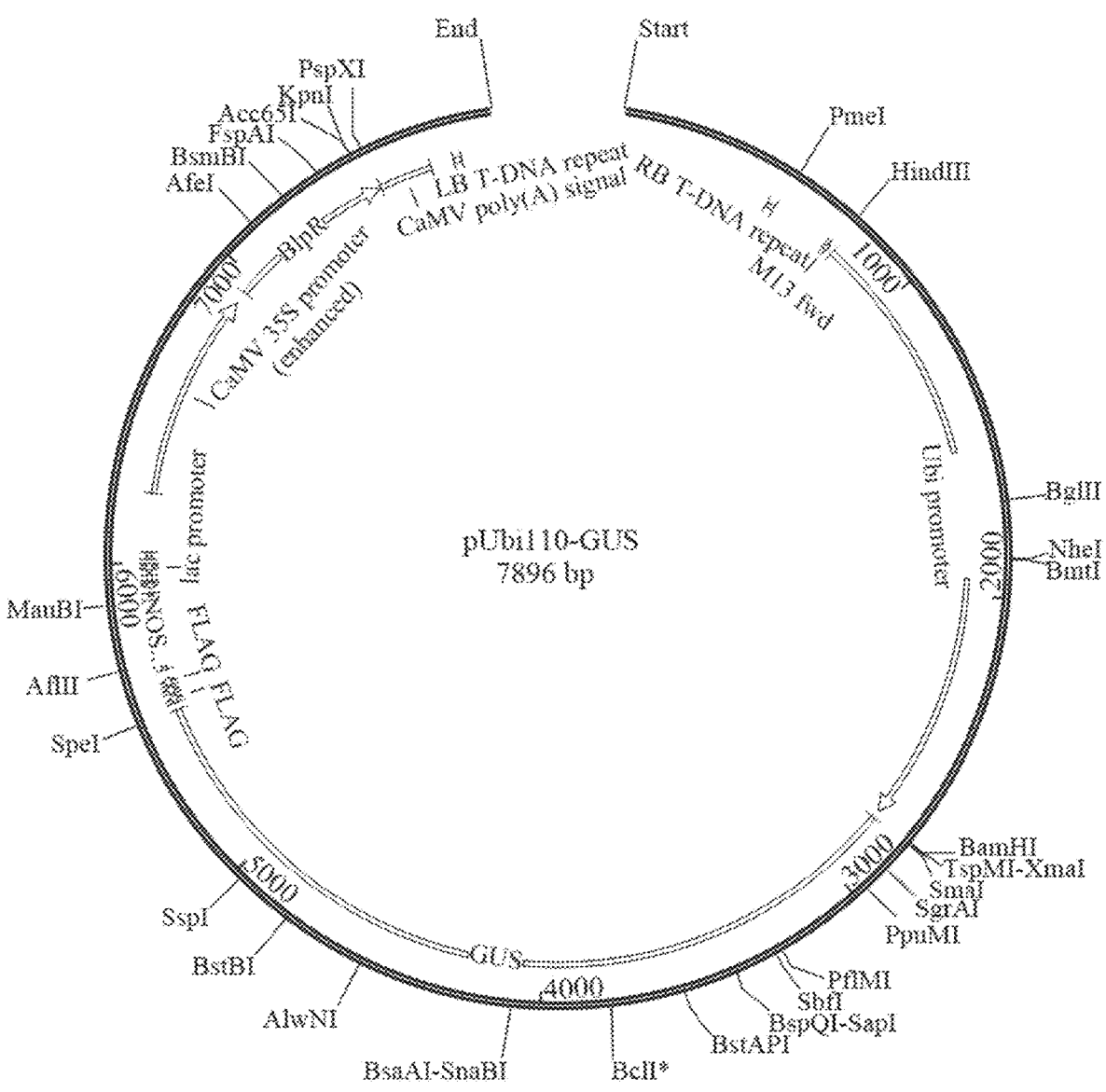
FIG. 2 shows a vector structure diagram of the of a plant expression vector pUbi110-GUS.
Figure 3A:
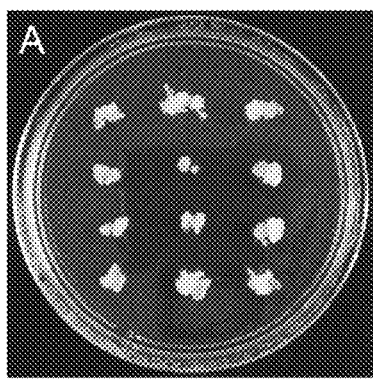
FIGS. 3A-3D shows transgenic resistant plants obtained by transforming immature embryo explants of wheat of different genotypes with plant expression vectors pUbi110-TaHRF2 and pUbi110-GUS.
Figure 3B:
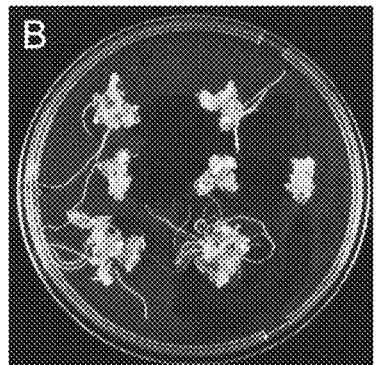
Figure 3C:
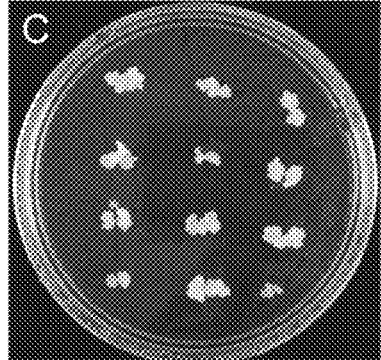
Figure 3D:
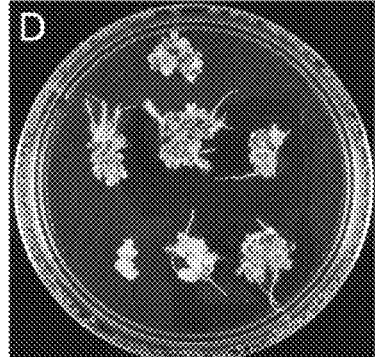

The amplified PCR product was ligated to an enzyme cleavage product of a pUbi110 vector by referring to homologous recombination steps of LightNing™ DNA Assembly Mix Plus (BestEnzymes Biotech Co., Ltd.), and sequencing was performed. Plasmids were extracted from monoclonal colonies with correct sequencing by referring to a FastPure Plasmid Mini Kit (Nanjing Vazyme Biotech Co., Ltd., catalog number: DC201-01), and a pUbi110-GUS was obtained. A structure diagram of the vector is as shown in FIG. 2.

Example 2: *Agrobacterium*-Mediated Transformation of Wheat Immature Embryos and Investigation of Effects I. Transformation of Wheat Immature Embryos Using an *Agrobacterium*-Mediated Method:

Wheat (*Triticum aestivum* L.) Transformation Using Immature Embryos (Ishida et al., 2015) was referred to for detailed steps and procedures of the *Agrobacterium*-mediated method for wheat immature embryos. Basic steps for genetic transformation were as follows:

The recombinant expression vector pUbi110-TaHRF2 constructed in Example 1 was transformed into an *Agrobacterium* EHA105 competent cell, and an *Agrobacterium* strain available for transformation was obtained, which was named pUbi110-TaHRF2/EHA105. The pUbi110-GUS vector constructed in Example 1 was transformed into an *Agrobacterium* EHA105 competent cell, and an *Agrobacterium* strain available for transformation was obtained, which was named pUbi110-GUS/EHA105.

Three days before infection, the *Agrobacterium* strains pUbi110-TaHRF2/EHA105 and pUbi110-GUS/EHA105 were separately inoculated on a YEP solid medium containing 50 mg/L kanamycin and 50 mg/L rifampicin, and then cultured in an incubator at 28° C. in the dark for 2 days. Single colony was picked and inoculated in a YEP liquid medium containing 50 mg/L kanamycin and 50 mg/L rifampicin, and cultured at 28° C. with overnight shaking at 220 rpm. The above *Agrobacterium* solutions were placed in 2 ml centrifuge tubes, and centrifuged at 6000 rpm for 5 minutes. The supernatants were discarded. The precipitates were resuspended with a resuspension to buffer obtain *Agrobacterium* resuspensions of pUbi110-TaHRF2/EHA105 and pUbi110-GUS/EHA105, respectively.

Immature embryos of wheat varieties "Beijing 8" and "Lumai 1" 14 days after anthesis were taken and infected with *Agrobacterium* resuspensions of pUbi110-TaHRF2/EHA105 and pUbi110-GUS/EHA105, respectively. The infected immature embryos were placed with the scutellum upwards on a WLS-AS medium (1/10 MS basal medium, 1/10 MS vitamins, 10 g/L glucose, 100 µM acetosyringone, 8 g/L agarose), and cultured in an incubator at 23° C. in the dark for 2 days.

The co-cultured immature embryos were transferred to a WLS-Res medium (MS basal medium, MS vitamins, 0.5 mg/L 2,4-D, 2.2 mg/L picloram, 0.5 g/L glutamine, 0.1 g/L casein, 0.75 g/L MgCl$_2$·6H$_2$O, 40 g/L maltose, 0.85 mg/L AgNO$_3$, 100 mg/L vitamin C, 250 mg/L carbenicillin, 5 g/L agarose), and cultured in an incubator at 25° C. in the dark for 5 days.

The calli after the recovery culture were transferred to a WLS-P5 medium (WLS-Res medium supplemented with 5 mg/L phosphinothricin (PPT)), and cultured in an incubator at 25° C. in the dark for 14 days.

A resulting calli were then transferred to a WLS-P10 medium (WLS-Res medium supplemented with 10 mg/L PPT), and cultured in an incubator at 25° C. in the dark for 21 days.

The above calli were transferred to an LSZ-P5 medium (MS basal medium, LS vitamins, 5 mg/L zeatin, 20 g/L sucrose, 250 mg/L carbenicillin, 5 mg/L PPT, 3 g/L phytagel), and cultured in an incubator at 25° C. under light conditions for 14 days (FIGS. 3A-D).

Figure 4:
FIG. 4 shows candidate transgenic plants obtained by infecting wheat with a plant expression vector pUbi110-TaHRF2.

Regenerated shoots of wheat calli were transferred to an LSF-P5 medium (MS basal medium, LS vitamins, 0.2 mg/L IBA, 15 g/L sucrose, 250 mg/L carbenicillin, 5 mg/L PPT, 3 g/L phytagel), and cultured in an incubator at 25° C. under light conditions until the root length of the regenerated shoots reached about 1-2 centimeters (FIG. 4).

The robust rooted seedlings were transplanted into nutrient soil, and resistant seedlings of pUbi110-TaHRF2 and pUbi110-GUS were obtained.

Figure 5:
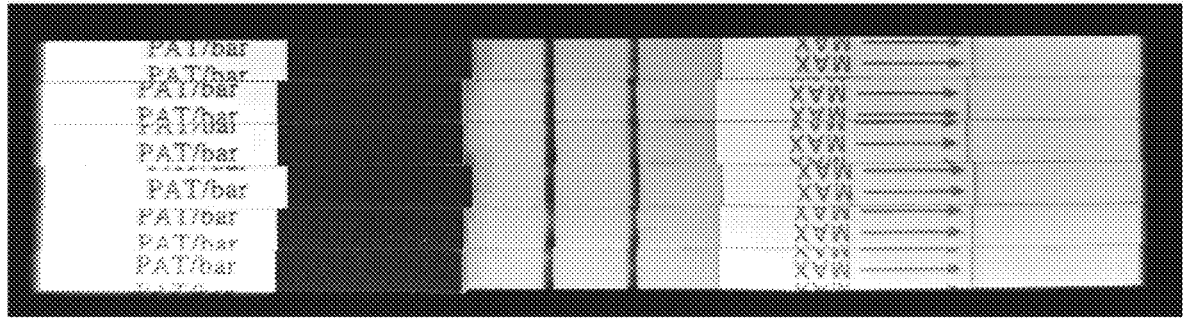
FIG. 5 shows the results of a rapid detection by PAT/bar strips for candidate transgenic plants transformed with a plant expression vector pUbi110-TaHRF2.

II. Rapid Detection by PAT/Bar Test Strips and PCR Identification of Candidate Transgenic Plants 1. The resistant plants were detected using PAT/bar rapid test strips (catalog number: AA1032-LS, Shanghai Youlong Biotechnology Co., Ltd.). Specific steps were as follows: An appropriate amount of leaf tissue from candidate transgenic wheat plants was cut and placed in a 1.5 ml centrifuge tube. The leaves were crushed by rotational grinding using a grinding pestle. After continuously pressing for 20-30 seconds, 0.20 ml (about 8 drops) of extraction buffer was added. The crushing step was repeated to ensure that the sample and the extraction buffer were fully contacted and mixed. The pestle was removed. Rapid test strips were taken out of a test strip bucket and inserted directly into a sample tank (the level of the liquid to be tested was not allowed to exceed the MAX arrow line). The timing was started. The results were supposed to be read in 5-8 minutes, and any reading beyond that time limit was considered invalid. The results of the detection by the rapid test strips are shown in FIG. 5.

2. Genomic DNA of leaf was extracted from wheat plants of the TO generation transformed with pUbi110-TaHRF2 and pUbi110-GUS vectors using a Cetyltrimethylammonium Bromide (CTAB) method (Sambrook and Russell, Molecular Cloning: A Laboratory Manual, 2001). Primers were designed to detect the bar gene. Sequences of the primer pair (upstream primer: 5'-GGCGGTCTGCAC-CATCGTCAACCACTAC-3' (SEQ ID NO:11); downstream primer: 5'-AGTCCAGCTGCCAGAAACCCACGTCATG-3' (SEQ ID NO:12)) were given, and the length of the amplified sequence was 446 bp. An amplification system consisted of 1 µl of upstream primer (10 µmol/µl), 1 µl of downstream primer (10 µmol/µl), 10 µl of 2× Rapid Taq Master Mix, 1 µl of cDNA template, and a balance of ddH$_2$O to 20 µl. Amplification conditions were: predenaturation at 95° C. for 5 minutes; denaturation at 95° C. for 30 seconds, annealing at 58° C. for 30 seconds, extension at 72° C. for 15 seconds, for 35 cycles; extension at 72° C. for 5 minutes.

Figure 6:
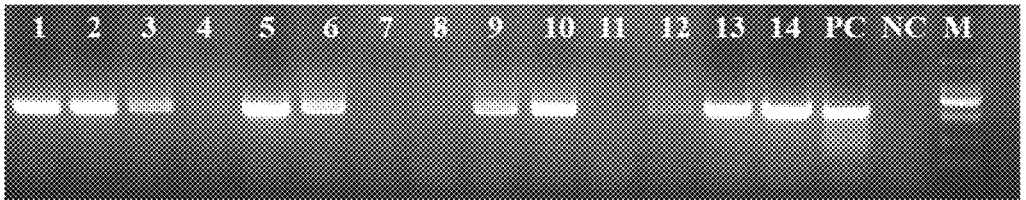
FIG. 6 shows the results of PCR-specific amplification of a bar gene in candidate transgenic plants obtained by infecting wheat with a plant expression vector pUbi110-TaHRF2; in the figure, 1-7 represent candidate transgenic plants of Beijing 8 after infection, 8-14 represent candidate transgenic plants of Lumai 1 after infection, PC represents a positive plasmid, NC represents a negative control, and M represents a 2000 bp molecular weight marker.

The PCR identification results are shown in FIG. 6. There was no 446 bp bar gene fragment in non-transgenic and wild-type wheats.

III. Statistics of Genetic Transformation Efficiency of Different Wheat Genotypes After infection of the wheat immature embryos with *Agrobacterium*, the calli induced to form were screened. When they were transferred to the LSF-P5 medium, the number of differentiated resistant calli formed was counted. After PCR identification, the number of positive seedlings was counted. Finally, the differentiation efficiency of resistant calli and the transformation efficiency were calculated according to the following formulas:

differentiation efficiency of resistant *calli* (%) = (number of differentiated resistant *calli* ÷ total number of immature embryos) × 100%;

transformation efficiency (%) = (number of positive seedlings ÷      5 total number of immature embryos) × 100%;

The transformation of the pUbi110-TaHRF2 vector could effectively increase the transformation efficiency of wheat compared with the control vector pUbi110-GUS. The results are as shown in Table 1.

TABLE 1

| | | Total number of immature embryos | Number of differentiated resistant calli | Number of calli with positive seedlings | Differentiation efficiency of resistant calli (%) | Transformation efficiency (%) |
|---|---|---|---|---|---|---|
| Genotype | Vector | | | | | |
| Beijing 8 | pUbi110-TaHRF2 | 70 | 62 | 21 | 88.57% | 30.00% |
| | pUbi110-GUS | 117 | 14 | 0 | 11.97% | 0% |
| Lumai 1 | pUbi110-TaHRF2 | 127 | 85 | 19 | 66.93% | 14.96% |
| | pUbi110-GUS | 105 | 4 | 0 | 3.81% | 0.00% |

Comparison of transformation efficiency of the control vector pUbi110-GUS and the pUbi110-TaHRF2 vector Using the immature embryos of the wheat variety Beijing 8 as explants for genetic transformation, the differentiation efficiency and the transformation efficiency of the resistant calli from the transformation of the pUbi110-TaHRF2 vector were 88.57% and 30.00%, respectively, both of which were much higher than the 11.97% differentiation efficiency of the resistant calli during the transformation of the control vector pUbi110-GUS. Moreover, no transgenic plants could be obtained during the transformation of the control vector. When genetic transformation was performed using Lumai 1 as a donor plant, the differentiation efficiency of the resistant calli from the transformation of the pUbi110-TaHRF2 vector and the control vector pUbi110-GUS were 66.93% and 3.81%, respectively, and the transformation efficiency of the pUbi110-TaHRF2 vector was 14.96%. Neither could positive transgenic plants be obtained with the control vector pUbi110-GUS. Positive plants obtained from the transformation of the pUbi110-TaHRF2 vector grew and developed normally.

As can be seen from the above results, the TaHRF2 gene could significantly improve the transformation efficiency of wheat and partially solve the problem of genotype dependence in the genetic transformation of wheat.

The examples described above are only some embodiments of the present application and are not intended to limit the present application. For those skilled in the art, various changes and variations may be made to the present application. Any modification, equivalent, improvement, etc., made within the spirit and principles of the present application, should be encompassed in the scope of protection of the present application.

What is claimed is:

1. A method for boosting transformation efficiency of wheat using *Agrobacterium*-mediated transformation, the method comprising:

ligating a TaHRF2 gene into an expression vector to construct a recombinant expression vector, and transforming the recombinant expression vector into an *Agrobacterium* competent cell to obtain an *Agrobacterium* strain for use in transformation; and infecting a wheat immature embryo with the *Agrobacterium* strain, thereby boosting transformation efficiency and obtaining a wheat transgenic and gene-edited plant;

wherein the TaHRF2 gene is a DNA molecule selected from the group consisting of i) and ii) below:

i) the DNA molecule having the nucleotide sequence set forth in SEQ ID NO: 1; and ii) the DNA molecule encoding the amino acid sequence set forth in SEQ ID NO: 2;

wherein the wheat is of variety "Beijing 8" or "Lumai 1".

2. The method of claim 1, wherein the expression vector is a pUbi110 plasmid.

3. The method of claim 1, wherein the *Agrobacterium* competent cell is *Agrobacterium* EHA105.

4. The method of claim 1, wherein a protein encoded by the TaHRF2 gene is a protein selected from the group consisting of (A1) and (A2) below:

(A1) the protein consisting of the amino acid sequence set forth in SEQ ID NO: 2 of the Sequence Listing; and (A2) a fusion protein obtained by attaching a protein tag to the N-terminus and/or the C-terminus of the protein defined in (A1).

* * * * *

SEQUENCE LISTING

```
Sequence total quantity: 12
SEQ ID NO: 1            moltype = DNA  length = 792
FEATURE                 Location/Qualifiers
source                  1..792
                        mol_type = other DNA
                        note = TaHRF2 gene
                        organism = synthetic construct
SEQUENCE: 1
atggcggcga cggcgactgc gacggcggcg gcgacgagcg tggtgacggg gacgacgcgg  60
tggtgcccga cgccggagca gctgatgatc ctggaggaga tgtaccgcgg cgggctgcgc  120
acccccaacg cgtcgcagat ccagcagatc acggcgcacc tggcccacta cggccgcatc  180
gagggcaaga acgtcttcta ctggttccag aaccacaagg cccgggaccg ccagaagctc  240
cgccgcaggc tctgcatgag ccaccacctc ctctcctgcg cgcactacta cgccgccgcc  300
aacgccggcc agtaccacca gcagcagcag ctcctcggcg ccggcgcggt gcctcctccg  360
ctgctgcagc acccgcagca gcagcagtac tactccgcct cttgcgccgg tggcggctac  420
gaccagcacc tgctcccgac gaccgtccca gcttccgctt acgctgctgc tgctgggtac  480
gcctacccct tcgccggcgt gccggcaagc cggtgcgccg agccctcgcc gccaaacacc  540
ccgctctcct tccatcatca gggaggaggc gtagtgggat cgccggagta ctcgctgggg  600
aggctgggca acttcggcgt ggtggaggac acatgccggc cgtcgcggta cgagcagcag  660
ccgcagcagc tggccgcggc gacggaagat caggcggcgc cggtgacggc gacggggctg  720
```

-continued

```
ttctgccggc cgctgaagac gctggacctc ttccccggcg cgatcaagga ggagcagcgc    780
gacgtcgcct ag                                                        792

SEQ ID NO: 2               moltype = AA  length = 263
FEATURE                    Location/Qualifiers
source                     1..263
                           mol_type = protein
                           note = Protein encoded by the TaHRF2 gene
                           organism = synthetic construct
SEQUENCE: 2
MAATATATAA ATSVVTGTTR WCPTPEQLMI LEEMYRGGLR TPNASQIQQI TAHLAHYGRI    60
EGKNVFYWFQ NHKARDRQKL RRRLCMSHHL LSCAHYYAAA NAGQYHQQQQ LLGAGAVPPP    120
LLQHPQQQQY YSASCAGGGY DQHLLPTTVP ASAYAAAAGY AYPFAGVPAS RCAEPSPPNT    180
PLSFHHQGGG VVGSPEYSLG RLGNFGVVED TCRPSRYEQQ PQQLAAATED QAAPVTATGL    240
FCRPLKTLDL FPGAIKEEQR DVA                                            263

SEQ ID NO: 3               moltype = DNA  length = 19
FEATURE                    Location/Qualifiers
source                     1..19
                           mol_type = other DNA
                           note = Upstream primer of a cDNA
                           organism = synthetic construct
SEQUENCE: 3
atggcggcga cggcgactg                                                 19

SEQ ID NO: 4               moltype = DNA  length = 19
FEATURE                    Location/Qualifiers
source                     1..19
                           mol_type = other DNA
                           note = Downstream primer of a cDNA
                           organism = synthetic construct
SEQUENCE: 4
ctaggcgacg tcgcgctgc                                                 19

SEQ ID NO: 5               moltype = DNA  length = 39
FEATURE                    Location/Qualifiers
source                     1..39
                           mol_type = other DNA
                           note = Upstream primer of pEASY-Blunt3-TaHRF2 plasmid
                           organism = synthetic construct
SEQUENCE: 5
cgactctaga ggatccccgg gatggcggcg acggcgact                          39

SEQ ID NO: 6               moltype = DNA  length = 39
FEATURE                    Location/Qualifiers
source                     1..39
                           mol_type = other DNA
                           note = Downstream primer of pEASY-Blunt3-TaHRF2 plasmid
                           organism = synthetic construct
SEQUENCE: 6
gaattccggc tcgagactag tctaggcgac gtcgcgctg                          39

SEQ ID NO: 7               moltype = DNA  length = 18
FEATURE                    Location/Qualifiers
source                     1..18
                           mol_type = other DNA
                           note = Upstream primer of nucleotides at positions
                            15108-16919 of Gene ID: MN266288.1 on the NCBI
                           organism = synthetic construct
SEQUENCE: 7
atgttacgtc ctgtagaa                                                 18

SEQ ID NO: 8               moltype = DNA  length = 18
FEATURE                    Location/Qualifiers
source                     1..18
                           mol_type = other DNA
                           note = Downstream primer of nucleotides at positions
                            15108-16919 of Gene ID: MN266288.1 on the NCBI
                           organism = synthetic construct
SEQUENCE: 8
tcattgtttg cctccctg                                                 18

SEQ ID NO: 9               moltype = DNA  length = 45
FEATURE                    Location/Qualifiers
source                     1..45
                           mol_type = other DNA
                           note = Upstream primer of pEASY-Blunt3-GUS
                           organism = synthetic construct
SEQUENCE: 9
```

-continued

```
cgactctaga ggatccccgg gatgttacgt cctgtagaaa cccca                   45

SEQ ID NO: 10          moltype = DNA  length = 40
FEATURE                Location/Qualifiers
source                 1..40
                       mol_type = other DNA
                       note = Downstream primer of pEASY-Blunt3-GUS
                       organism = synthetic construct
SEQUENCE: 10
gaattccggc tcgagactag tttgtttgcc tccctgctgc                         40

SEQ ID NO: 11          moltype = DNA  length = 28
FEATURE                Location/Qualifiers
source                 1..28
                       mol_type = other DNA
                       note = Upstream primer for detecting the bar gene
                       organism = synthetic construct
SEQUENCE: 11
ggcggtctgc accatcgtca accactac                                      28

SEQ ID NO: 12          moltype = DNA  length = 28
FEATURE                Location/Qualifiers
source                 1..28
                       mol_type = other DNA
                       note = Downstream primer for detecting the bar gene
                       organism = synthetic construct
SEQUENCE: 12
agtccagctg ccagaaaccc acgtcatg                                      28
```